US005750787A

United States Patent [19]

Lai et al.

[11] Patent Number: 5,750,787
[45] Date of Patent: May 12, 1998

[54] LIQUID ALKYLATED DIPHENYLAMINE ANTIOXIDANT

[75] Inventors: John T. Lai, Broadview Heights; Deborah S. Filla, Twinsburg, both of Ohio

[73] Assignee: B. F. Goodrich Company, Richfield, Ohio

[21] Appl. No.: 655,511

[22] Filed: May 30, 1996

Related U.S. Application Data

[63] Continuation-in-part of Ser. No. 527,475, Sep. 13, 1995, Pat. No. 5,672,752.

[51] Int. Cl.$^6$ .................................................. C07C 209/02
[52] U.S. Cl. .................................. 564/409; 564/433
[58] Field of Search .................................. 564/409, 433

[56] References Cited

U.S. PATENT DOCUMENTS

| 2,943,112 | 6/1960 | Popoff et al. |
|---|---|---|
| 3,452,056 | 6/1969 | Sundholm |
| 3,655,559 | 4/1972 | Holt |
| 4,824,601 | 4/1989 | Franklin |

OTHER PUBLICATIONS

Chemical Reactions on Clays by Pierre Laszlo in Science vol. 235, pp. 1473–1477, published by American Association for the Advancement of Science, Washington, D.C., Mar., 1987.

*Primary Examiner*—Brian M. Burn
*Attorney, Agent, or Firm*—Mary Ann Tucker; Samuel B. Laferty

[57] ABSTRACT

A process for monoalkylating diphenylamine using a clay catalyst is disclosed which results in a reaction product having substantial amounts of desirable monoalkylated diphenylamine and minimal amounts of less desirable disubstituted diphenylamine and unsubstituted diphenylamine. The disclosed process uses clay catalysts which favor monoalkylation over dialkylation and specific conditions such as reaction temperature, mole ratios of alkylating olefin to diphenylamine, reaction times, and catalyst amounts. Preferred olefins are diisobutylene and linear alpha olefins having from 6 or 8 to 18 carbon atoms. When more than 1 wt. % residual unreacted diphenylamine is present it may be converted to alkylated diphenylamine by reacting with styrene, alpha-methylstyrene or isobutylene.

11 Claims, No Drawings

LIQUID ALKYLATED DIPHENYLAMINE ANTIOXIDANT

CROSS-REFERENCE

This application is a continuation-in-part of U.S. application Ser. No. 08/527,475, filed Sep. 13, 1995, now U.S. Pat. No. 5672752 for "Liquid Alkylated Diphenylamine Antioxidant.

FIELD OF THE INVENTION

A process for alkylating diphenylamine which results in high amounts of desirable monosubstituted diphenylamine antioxidants is described. These monoalkylated diphenylamines have good antioxidant activity in various lubricating oils and polymeric molding compositions. These antioxidants are low in yellow color, resist further yellowing and are liquid at 25° C.

BACKGROUND OF THE INVENTION

U.S. Pat. No. 2,943,112 ('112) teaches that alkylated diphenylamines are useful as antioxidants (AO). Therein it describes the alkylation of diphenylamine with relatively unreactive olefins, such as secondary alkenes (column 4, line 9–23), followed by an alkylation reaction with more reactive olefins to scavenge the unreacted diphenylamine to a concentration of less than 3%. This avoided the necessity of distilling out the undesirable unsubstituted diphenylamine. The reference mentions clay and other alkylation catalysts. Although clay offers some other processing advantages (e.g. easier separation of the catalyst from the product) the reference doesn't differentiate between the alkylation catalysts based on the relative proportions of mono and disubstituted diphenylamine in the reaction products.

As disclosed in U.S. Pat. No. 2,943,112 column 2, lines 26–29, monoalkylated diphenylamine is believed to be more reactive than unsubstituted diphenylamine in alkylation reactions. It was difficult to get high amounts of monoalkylated diphenylamine because as soon as the diphenylamine was monoalkyled it soon thereafter was dialkylated minimizing the amount of monoalkylated diphenylamine.

The use of clay as catalyst in the alkylation of diphenylamine is disclosed in U.S. Pat. No. 3,452,056 which describes the alkylation of diphenylamine with alpha-methyl styrene and related olefins with clay as the catalyst. In the prior art, clay was mentioned as having the advantage of giving lighter colored product and being easy to remove by filtration after the reaction. As a catalyst, clay and other Lewis Acids, such as $AlCl_3$ or $BF_3$ (column 4, line 57–69) are generally taught as being interchangeable.

U.S. Pat. No. 4,824,601 ('601) teaches that liquid antioxidants are desirably (column 1, line 26–33) prepared from diphenylamine and diisobutylene at reaction temperatures above 160° C. (abstract). At the high temperatures, the octyl group was cracked to give a butyl group and perhaps unsubstituted diphenylamine itself (column 2, line 66–68). The high temperature alkylation was continued until less than 25% dioctyldiphenylamine (DOD) was present. When diisobutylene is the alkylating olefin and the temperature is above 160° C. substantial amounts of dioctyldiphenylamine are produced. Dioctyldiphenylamine is a liquid at the alkylation temperature, but when present above 20 or 25 wt. % in the product at room temperature, it results in a solid product which is more difficult to handle or transport since it cannot be pumped from the reactor.

Unsubstituted diphenylamine is less desirable as an antioxidant because it sensitizes human skin to other irritants and tends to yellow in the composition in which it is used. High vacuum distillation can separate unsubstituted, monosubstituted, and polysubstituted diphenylamines but this is an expensive and time consuming process step.

SUMMARY OF INVENTION

A process for alkylating unsubstituted diphenylamine is disclosed which selectively causes a higher proportion of monoalkylsubstitution and produces lower amounts of less desirable unsubstituted diphenylamine and/or disubstituted or polysubstituted diphenylamines than the prior art. The process uses a clay catalyst (which has greater selectivity in alkylation reactions than other alkylation catalysts) and generally uses milder conditions (e.g. lower temperatures or shorter times). Disclosed olefins that result in higher proportions of monoalkylsubstitution are diisobutylene and $C_6$–$C_{18}$ linear olefins with unsaturation between the first and second carbon atom.

DETAILED DESCRIPTION

A process is described for making liquid and highly active antioxidants (AOs) from the alkylation of diphenylamine (DPA) with two commonly known and inexpensive classes of olefins, namely diisobutylene (DIB) and the linear alpha-olefins. Commercially available diphenylamine is generally free of alkyl substituents. However alkyl substituents do not interfere with subsequent alkylation so the source of diphenylamine may contain small amounts (e.g. up to 2, 5, 10 or 20 wt. %) of alkylated diphenylamine.

Although alkylation with diisobutylene generally results in a solid product when greater than 25 wt. % dioctyl DPA is formed, special method limitations of the present invention solve this problem. Unexpectedly diphenylamine can be selectively alkylated with DIB at a temperature lower (e.g. less than 160° C.) than the cracking temperature of octyl groups (160°–250° C.) or for shorter periods of time (e.g. less than 5 hrs. or less than 3 hrs), with a clay catalyst, to give a product mixture with less than 25% dioctyldiphenylamine (DOD), less than 25% DPA and greater than 50% or 55% by weight monooctyldiphenylamine (MOD) based on the total weight of the diphenylamine and alkylated DPA.

Alternatively, when alkylating with the relatively unreactive linear alpha-olefins (a secondary alkene with terminal unsaturation as defined in U.S. Pat. No. 2,943,112, column 4, line 9–13), one can either make high amounts of dialkyl DPA along with low amounts of unreacted DPA by using large excess of linear alphaolefin, or one can make high amounts of monoalkyl DPA and high amounts of unreacted DPA by using deficient amount of olefin.

Monoalkylated diphenylamines are very desirable for use as antioxidants. As disclosed in U.S. Pat. No. 2,943,112 column 1, lines 28–34, if the alkyl group has six or more carbon atoms the monoalkylated diphenylamine will be low in yellow color and will resist yellowing. Di or polysubstituted diphenylamines are less effective than monosubstituted diphenylamines on a weight basis because additional alkylation significantly reduces the number of moles of diphenylamine per gram. For example diphenylamine weighs 169 g/mole, monooctyldiphenylamine weighs 281 g/mole and dioctyldiphenylamine weighs 393 g/mole.

As set forth in the background it is desirable to remove most of the unreacted (non alkylated) diphenylamines before the reaction product is used as an antioxidant. As set forth later the unreacted diphenylamine may be reacted with more reactive olefin(s) (isobutylene, styrene and/or alpha-methylstyrene) to convert residual unreacted diphenylamine to alkylated diphenylamine.

Clay usually results in a lower degree of yellow color in the alkylated product than other alkylation catalysts because clay preferentially absorbs colored species. The clay is preferably an acid activated bentonite clay. Clay is thought to require higher temperatures and/or longer reaction times than $AlCl_3$ and related catalysts.

It has unexpectantly been found that clay (e.g. acid activated bentonite clay) when used as a catalyst for alkylating diphenylamine results in proportionally more monoalkylated diphenylamine than the other alkylation catalysts such as $AlCl_3$, $BF_3$, $Et_2O$, and $SbCl_3$. When the particular olefin used and the other reaction conditions are optimized the amount of desirable monoalkylated diphenylamine can be substantial and the amounts of less desirable unsubstituted and polysubstituted diphenylamine can be kept low.

These desirable percentages of products are a result of the clay catalysts preferentially catalyzing the alkylation reaction of the unsubstituted diphenylamine rather than the further alkylation of monoalkyldiphenylamine. The tetrahedral and octahedral layers of clay specifically and precisely repeated are believed to offer less access to the monoalkyldiphenylamine molecule with its bulky tertiary octyl groups than the unsubstituted diphenylamine molecule to the reactive sites in the catalysts. The monoalkylated diphenylamine is formed is converted to dialkylated or polyalkylated diphenylamine at a slower rate with clay catalyst than with other catalysts allowing the concentration of monoalkylated diphenylamine to increase in the reaction product. Note that by specifying clay catalyst the use of amounts of $AlCl_3$, $ZnCl_3$, $SnCl_4$, $H_3PO_4$, $BF_3$ or other alkylation catalysts other than acidified clay is restricted to those amounts that would be ineffective to cause 10 percent or more of the total alkylation under the conditions specified.

The clays useful in alkylation reaction of diphenylamines are those used for bleaching oils and waxes. These are often referred to as acid activated clays. Preferred clays are sub-bentonites or bentonites which are characterized by rapid slaking when it is in the air dried state and only a slight swelling when placed in water. They consist predominantly of the clay mineral montmorillonite. The clay can be used in alkylation reactions in amounts from about 0.5 or 1 wt. % to about 60 percent and, and in one embodiment more desirably from about 2 to about 20 wt. % based on the amount of unsubstituted diphenylamine used as a reactant. In another embodiment the clay is from about 0.5 to about 4 or 5 weight %, more desirably from about 1 to about 3 weight percent based upon the amount of unsubstituted diphenylamine used as a reactant.

Commercially available clay catalysts include Filtrol™ and Retrol™ available from Engelhard; Fulcat™ 14, Fulmont™ 700C, Fulmont™ 237, and Fulcat™ 22B available from Laporte Industries; and Katalysator™ K10 available from Sud-Chemi. These clays may include acid activated or acid leached clays. Acid activated clays are preferred. The clay catalysts may contain some water as received. Removal of the water prior to use results in a lighter colored reaction product. Therefore it is desirable to use a low water content clay or to remove the water by heating the clay with a nitrogen sweep or with vacuum stripping.

Clays are aluminosilicates. The aluminum III cations are bonded to an octahedral arrangement of oxygen anions. Repetition of these $AlO_6$ units in two dimensions formed an octahedral layer. Likewise a tetrahedral layer is formed from $SiO_4$ silicate units. Clays are classified according to the relative number of tetrahedral and octahedral layers. Montmorillonite clays, which have been used in organic chemical applications, have a octahedral layer sandwiched between two tetrahedral layers.

When the alkylation olefin is diisobutylene (DIB) the alkylation temperature in a first embodiment is desirably from about 105°, 110° or 120° C. to about 195° or 200° C. The reaction rate varies with time.

When the alkylation with diisobutylene is carried out at from 105°, 110° or 120° C. to less than 160° C. (e.g. to less than 155° C., 157° C. or 159° C.), more desirably from about 105°, 110° or 120° C. to about 145° or 150° C., the reaction time is desirably from about 1 hour to about 5 hours, more desirably from about 2 to about 4 hours. The low reaction temperature minimizes the cracking of diisobutylene or octyl groups to butyl groups.

When the alkylation is carried out at a temperature from above 160° C. (e.g. from about 160°, 161° or 162° to about 185°, 190°, 195° or 200° C.) more desirably from about 170° to about 185° or 190° C. then the reaction times are desirably less than 5 hrs, more desirably less than 3 hrs, preferably less than 2 hrs and more preferably less than 1 hr. The reaction at this temperature generally is from about 15 or 30 minutes to about 2 hours. At either temperature range the reaction time is desirably less than 2, 3 or 5 hours. The shorter reaction times result in less cracking of the diisobutylene or octyl groups to butyl groups.

The unsubstituted diphenylamine or solution of unsubstituted diphenylamine used as a reactant desirably contains only low amounts of mono, di or polysubstituted (e.g. alkylated) diphenylamine prior to this alkylation reaction (e.g. less than 20 or 10 wt. % based on the total of unsubstituted, mono, di and polysubstituted diphenylamines). Preferably the initial unsubstituted diphenylamine used as a reactant is essentially free of (defined as less than 5 or 2 wt. %) these mono, di or polysubstituted diphenylamines components (i.e. meaning the DPA has not been alkylated with another olefin).

The addition of DIB to the alkylation reaction is desirably metered but may be batch, sequential or another addition method. In the alkylation reaction of diphenylamine with diisobutylene in the presence of clay the mole ratio of diisobutylene to diphenylamine is desirably from about 1:0.5 to about 1:1.6 and more desirably from about 1:0.6 to 1:1.2 and preferably from about 1:0.7, 1:0.95 or 1:1.0 to about 1:1.1, 1:1.25 or 1:1.6.

The disclosed process typically results in less than about 25 wt. % (e.g. about 5 or 10 to about 20 or 25 wt. %) or less than about 20 wt. % dioctyldiphenylamine; at least 50 or 55 wt. % monoalkyl diphenylamine (e.g. about 50 or 55 wt. % to about 75 or 90 wt. %) more desirably at least 60 or 65 wt. % (e.g. from about 60 or 65 wt. % to about 75 or 80 wt. %) of monoalkyldiphenylamine (desirably monooctyl diphenylamine); and less than about 25 wt. % (e.g. about 5 or 10 to about 25 wt. %) more desirably less than 15 or 20 (e.g. from about 5 or 10 to about 15 or 20 wt. %) of unsubstituted diphenylamine in the reaction product. When the total monoalkylated diphenylamine (desirably monooctyl diphenylamine) is at least 55, 60 or 65 wt. %, the total of the dioctyl and unsubstituted diphenylamine is less than 45, 40 or less than 35 wt. %. The monoalkylated diphenylamine is usually monooctyldiphenylamine but may include small amounts of other monoalkylated diphenylamines (e.g. less than 5 wt. %, e.g. 0.01 to about 5 wt. %) from chain scission of the diisobutylene or monooctyl or dioctyl groups. Monobutyl DPA is less than 5 wt. %, more desirably less than 3 wt. % and preferably less than 1 or 2 wt. %. The amount of trisubstituted DPA is also low such as less than 5 wt. %. Desirably the monobutylmonooctyl diphenylamine is less than 3, more desirably less than 2 and preferably less than 1 wt. % of the reaction product.

At the reaction temperatures above 160° C. it is desirable to more closely control the stoichiometry of the reactants. The ratios with little excess diisobutylene prevent the formation of too much diioctyl diphenylamine due to stoichiometric considerations.

The reaction product from reaction of diisobutylene with diphenylamine at temperatures from about 105 or 110° C. to about 200° C. can be further reacted with one or more unsaturated olefin(s) more reactive than diisobutylene in alkylation reactions of DPA to reduce the amount of residual diphenylamine. Unsaturated olefin(s) more reactive than diisobutylene include isobutylene, styrene, alphamethylstyrene and other such olefins reactive in alkylation. The more reactive olefin may be added to the same reactor after the reaction with diisobutylene has proceeded sufficiently. The more reactive olefin may be added after 50 mole %, more desirably 75 mole % and preferably 90 mole % of the diisobutylene has been reacted onto the diphenylamine. The excess diisobutylene can be removed prior to adding the more reactive olefin(s) or retained in the reactor and removed later. The more reactive olefin would react at least with the unreacted DPA resulting in a final product with less than 5 wt. %, more desirably less than 3 wt. %, still more desirably less than 2 wt. %, and preferably less than 1 wt. % unsubstituted DPA. If the more reactive olefin is isobutylene then monobutyldiphenylamine and monobutyl monooctyl diphenylamine is formed from the diphenylamine and monooctyl diphenylamine, respectively. Desirably, the amount of dibutyl and distyryl DPA formed is less than 20 wt. % and the amount of dioctyl DPA is less than 25 or 20 wt. %.

The alkylation reaction with diphenylamine and the more reactive olefin converts the residual of less than 25, 20, or 15 wt. % diphenylamine to alkylated diphenylamine. If a temperature above 160° C. is used the reaction time is desirably less than 30 minutes or 1 hour so that the amount of octyl group cracking to butyl groups is minimized.

The mole ratio of the second more reactive olefin to total diphenylamine (total of unsubstituted mono, di and polysubstituted) is desirably from about 1:5 to about 1:0.667 and more desirably from about 1:2 to 1:1.

This method of using two different olefins for forming diisobutylene alkylated diphenylamines is preferred over the process of U.S. Pat. No. 4,824,601 because more control over the ratio and placement of octyl and butyl/non-octyl groups is possible when the cracking of octyl groups is prevented. The amount of unsubstituted diphenylamine can be reduced to less than 5 wt. %, more desirably less than 2 wt. %, and preferably less than 1 wt. % by this two step alkylation with different olefins in the first and second step. The addition of a second non-octyl olefin limits the amount of dioctyldiphenylamine formed to less than about 25 wt. % or less than about 20 wt. % so that the reaction product remains a liquid.

Alternatively, linear alpha olefins may be reacted with the solution of unsubstituted diphenylamine in the presence of clay catalysts to produce a diphenylamine alkylated with linear alpha olefins. This reaction yields increased amounts of monoalkylated diphenylamine due to the use of clay catalysts. The linear alpha olefin can have from 6 or 8 to 18 carbon atoms and has a carbon to carbon double bond between the first and second carbon atoms of the molecule. Desirably the linear olefin has only one carbon to carbon double bond. It may be a single alpha olefin or a mixture of alpha olefins. The reaction temperature when using alpha olefins is desirable from about 130° to about 200° C., more desirably from about 140° to about 190° C., and preferably from about 160° to about 185° C. for at least one hour, more desirably from about 2 hours to about 10 hours, and preferably from about 4 to about 8 hours.

In the alkylation reaction of diphenylamine with linear alpha olefins in the presence of clay the mole ratio of linear alpha olefin:diphenylamine is desirably from about 1:1 to about 1:0.526 and more desirably from about 1:0.909 to about 1:0.556. Most desirably it is from 1:0.833 to 1:0.667.

The reaction of linear alpha olefins with diphenylamine in the presence of clay catalyst desirably results in at least about 50 wt. % (e.g. about 50 to about 95 wt. %), more desirably at least about 60 wt. % and preferably at least about 65 wt. % of monoalkyldiphenylamine based on the total diphenylamine and alkylated diphenylamine in the reaction product. Desirably it results in less than about 50 wt. % (e.g. about 5 to about 50 wt. %), more desirably less than about 40 wt. %, and preferably less than about 35 wt. % di and/or polysubstituted diphenylamines. Desirably the amount mole ratio of monoalkylated DPA:dialkylated DPA is greater than 1:1. Desirably it results in less than 5 wt. %, e.g. from about 0.01 to about 5 wt. %, more desirably from about 0.01 to about 2 wt. %, and preferably from about 0.01 to about 1 wt. % unsubstituted diphenylamine. Unlike dioctyldiphenylamine the disubstituted diphenylamines resulting from alkylation with linear α-olefins do not cause solidification of the alkylation reaction product when present at concentrations above 25 wt. %. The unsubstituted diphenylamine or solution of diphenylamines used as a reactant is as previously described.

In a preferred embodiment the relative amount of unsubstituted diphenylamine remaining after alkylation with linear α-olefins is low (lower than in the reaction using diisobutylene as the alkylating agent of diphenylamine). This low amount of unsubstituted diphenylamine is accomplished by creating more disubstituted diphenylamine which (as specified above) does not cause solidification in this alkylation reaction product. The addition of linear alpha olefins to the reaction is preferably batch but may be metered, sequential, or another addition method.

If greater than 1, 2, or 3 weight percent of unreacted diphenylamine remains in the reaction product of the linear alphaolefin(s) and diphenylamine, that reaction product may be further reacted with the more reactive olefin(s) (e.g., isobutylene, styrene and/or alphamethylstyrene) as previously set forth for the reaction product of diisobutylene with diphenylamine. Sufficient amounts of the more reactive olefin(s) and suitable reaction time and temperatures are used to result in less than 3, 2, or 1 wt. % unreacted diphenylamine.

Although solvents have been used in alkylation reactions it is preferred in this process to alkylate with minimal solvent (e.g. less than 5 wt. % solvent based on the mixture of olefin, diphenylamine, and clay) or no solvent at all.

The unreacted olefins may be removed from the reaction product by distillation. Similarly the unreacted diphenylamine may be removed by processes such as fractional distillation or vacuum distillation if necessary. The amount of unreacted diphenylamine is desirably less than about 2 or 3 wt. % in the final product. The clay can be removed by filtration or other known separation methods.

The alkylation reaction can be carried out in an autoclave if high pressures due to the vapor pressure of the olefin are anticipated. The pressure used for the reaction is primarily controlled by the olefin used and the reaction temperature. As the product is always liquid, the reactants and products may be pumped into and out of the reactor.

The commercial diisobutylene used in this disclosure can be prepared by polymerizing isobutylene. That product is predominantly a mixture of the following isomers:

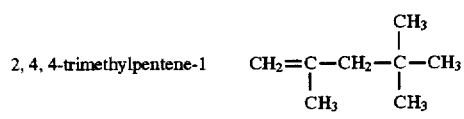

and

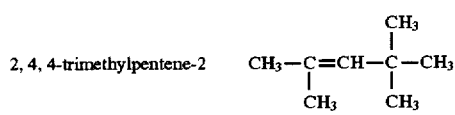

The first isomer being an alpha olefin is more reactive in alkylation reactions and is the majority of the diisobutylene and desirably is at least 60 wt. % of the diisobutylene.

The alkylated diphenylamine antioxidants of this disclosure are useful to stabilize natural source and synthetic source oils and polymers from oxidative degradation during processing reactions and in their final use as lubricants or articles. They may be used in combination with other antioxidants and additives.

The following examples show the alkylation reactions of diphenylamine with diisobutylene and with linear alpha olefins.

Control

U.S. Pat. No. 4,824,601 describes an alkylation reaction where one mole of diphenylamine (169 g) was combined with 1.75 mole of diisobutylene (196 g) and 33.8 g of clay catalyst and reacted at greater than 160° C. Apparently the dioctyldiphenylamine content initially exceeded 25% because the reaction was continued until the reaction product had less than 25 wt. % dioctyldiphenylamine as determined by gas chromatograph (column 7, lines 27–30). The product had unsubstituted diphenylamine, monoalkylated diphenylamine and alkylated diphenylamine where the alkyl groups were independently butyl or octyl. A sample of a commercial product believed to be made by the process of U.S. Pat. No. 4,825,601 was analyzed. The commercial sample had about 16.6% t-butyl DPA, 17.3% octyl DPA, 13.3% di-t-butyl DPA, 31.7% butyloctyl DPA, 16.1% dioctyl DPA, with the remainder being unsubstituted DPA or other polysubstituted DPA.

An experiment was performed to try and duplicate Examples 1–6 of U.S. Pat. No. 4,824,601 and characterize the relative amounts of the different alkyl substituted diphenylamines. Diphenylamine (67.7 g, 0.4 mole) and the acidic clay Retrol™ (13.5 g) were mixed in a 3-neck round bottom flask. It was stirred and heated at 165° C. Diisobutylene (78.6 g, 0.7 mole) was added slowly in 5 hrs. to keep the reaction temperature above 160° C. most of the time. After the addition, the reaction was kept at or above 160° C. for 19.5 hrs. GC analysis indicated that the product was composed of 2.8% diphenylamine, 12.9% butyldiphenylamine, 13.1% dibutyldiphenylamine, 13.1% octyldiphenylamine, 32.9% butyloctyldiphenylamine and 20.0% dioctyldiphenylamine. This example shows that a liquid alkylated diphenylamine can be formed by another method but the product is formed by chain scission of the diisobutylene or octyl groups into tertiary butyl substituents and results in a product having over 60% disubstituted DPA. In addition, this process of cracking octyl groups only works above 160° C.

EXAMPLE 1

One mole of diphenylamine (169 g) (DPA) was reacted with one mole of diisobutylene (DIB) (112 g) in the presence of an alkylation catalyst. The reaction product included DPA, MOD (monooctyldiphenylamine), and DOD (dioctyldiphenylamine).

1 DPA + DIB

+ catalyst→

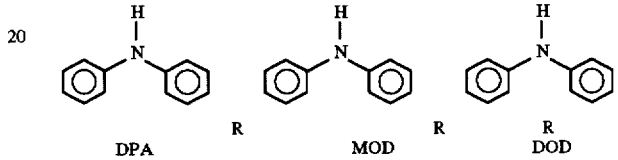

| CATALYST & | PRODUCT | | |
|---|---|---|---|
| CONDITIONS | DPA | MOD | DOD |
| 3% AlCl₃, 140° C., 1 hr | 23 WT % | 47 WT % | 30 WT % |
| 3% AlCl₃, 115° C., 2.5 hrs | 25 | 45 | 30 |
| 8% BF₃·Et₂O 115° C., 20 hrs | 24 | 50 | 26 |
| 3% SbCl₃, 140° C., 24 hrs | >95 | <5 | 0 |
| 2% Retrol™, 140° C., 2.5 hrs | 17 | 68 | 15 |

Retrol ™ is a clay catalyst.

This example shows that alkylation catalysts other than clay do not result in greater than 50 wt. % monoalkylated diphenylamine and simultaneously less than 25 wt. % dialkylated diphenylamine. As the amount of DOD is above 25 wt. % for the AlCl₃ and BF₃ catalysts further reaction or higher temperatures will only form more of the less desirable DOD. The maximum temperature with BF₃·Et₂O was 115° C. because that is the reflux temperature for BF₃·Et₂O. The SbCl₃ alkylation catalyst was not effective. The analysis of the product in this and subsequent examples was by gas chromatograph and was confirmed by mass spectrum analysis.

EXAMPLE 2

Diphenylamine (DPA) (0.2 mole) and Retrol™ (1 g) were placed in a 100 ml 3-neck flask. Diisobutylene (DIB) (24.6 g, 0.22 moles) was added dropwise at 150° C. under N₂ during an one hour period. The reaction was kept at 150° C. for 1.5 more hours (a sample taken and GC found it contained 12.7% DPA, 67.8% MOD and 17% DOD), then styrene (0.1 mole) was added over 5 minutes and the reaction was continued with heating at 150° C. for 1 hr. The reaction product was filtered with a buchner funnel and the filtrate was stripped of unreacted olefins by a simple distillation. The lightcolored product was found to contain ~1% unreacted diphenylamine with the rest mixed octylated and styrylated DPA. This example shows that styrene may be used as a scavenger olefin to react with unsubstituted DPA from the disclosed process.

EXAMPLE 3

One mole of DPA (169 g) and one mole of DIB (112 g) were reacted in the presence of Retrol™ (9.8 g) at 145° C. for 3 hours. The product of the reaction was analyzed to be 15 wt. % DPA, 70 wt. % MOD, and 15 wt. % DOD. That mixture of DPA, MOD, and DOD was further reacted with 0.6 mole of isobutylene for 1 hour at 145° C. The product of that reaction was analyzed to be less than 1 wt. % unsubstituted diphenylamine (DPA); 12 wt. % monobutyldiphenylamine (MBD); 6 wt. % dibutyldiphenylamine (DBD); 50 wt. % monooctyldiphenylamine (MOD); 12 wt. % butyl, octyldiphenylamine (BOD); and 15 wt. % dioctyldiphenylamine (DOD). The process of this disclosure is preferred due to the 1) lighter colored product than U.S. Pat. No. 4,824,601 2) lower amounts of olefins used and 3) less expensive process because the reaction temperature is lower. The alkyl substituents may also be controlled with respect to their type and amount allowing a more uniform product to be formed than as disclosed in U.S. Pat. No. 4,824,601.

EXAMPLE 4

Diphenylamine (169 g, 1 mole) diisobutylene (156.8 g, 1.4 mole) and Retrol™ clay (6.5 g) were mixed in an autoclave and heated to 140° C. After 3 hrs., GC analysis indicated that the reaction product consisted of approximately 15.5 wt. % diphenylamine (DPA), 71.4% monooctyldiphenylamine (MOD) and 12.3% dioctyldiphenylamine (DOD). Less than 1% of monobutylated diphenylamine was detected. A sample analyzed by GC after 4 hrs. of reaction showed that the product contains 8.3% DPA, 74.7% MOD and 15.7% DOD. Cracked product (butylated) was still less than 1%.

EXAMPLE 5

Diphenylamine (253.5 g, 1.5 mole), diisobutylene (168 g, 1.5 mole) and Retrol clay (14.75 g) were mixed in a 1 liter autoclave and heated to 185°–190° C. for 15 minutes. GC analysis showed that the reaction product consists of 18.8 wt. % of diphenylamine, 59.7% of monooctyl diphenylamine and 14.2% dioctyl diphenylamine. Less than 2% of monobutylated diphenylamine and less than 1% of monobutyl monooctyl diphenylamine was found.

EXAMPLE 6

Diphenylamine (253.5 g, 1.5 mole), diisobutylene (168 g, 1.5 mole) and Retrol™ clay (10.54 g) were mixed in a 1 liter autoclave and heated to 175°–180° C. for 1 hr. GC analysis showed that the product consists of 17.4 wt. % of diphenylamine, 66.0% of monooctyl diphenylamine and 12.8% dioctyl diphenylamine. Less than 1% of butylated diphenylamine was found.

EXAMPLE 7

Diphenylamine (253.5 g, 1.5 mole), diisobutylene (151.2 g, 1.35 mole) and Retrol™ clay (12.14 g) were mixed in a 1 liter autoclave and heated to 175–180° C. for 1 hr. GC analysis showed that the product consists of 19.8 wt. % of diphenylamine, 67.6% of monooctyl diphenylamine and 11.2% dioctyl diphenylamine. Less than 1% of butylated diphenylamine was found.

EXAMPLE 8

DPA (0.1 mole, 16.9 g) was reacted with 1-tetradecene (0.133 mole, 26.1 g) in the presence of a catalyst (Retrol™ clay or AlCl$_3$) to form unsubstituted diphenylamine (DPA) monoalkylated diphenylamine (M14D) and dialkylated diphenylamine (D14D) where the alkyl group was tetradecane.

| CATALYST & REACTION CONDITIONS | PRODUCT | | |
|---|---|---|---|
| | DPA | M14D | D14D |
| 3.0 g Retrol ™, 175–180° C., 6 hrs | <1 WT % | 69.9 WT % | 30.1 WT % |
| 1.3 g AlCl$_3$, 150° C., 8 hrs | 12.9 | 45.9 | 41.2 |
| 1.3 g AlCl$_3$, 175–180° C., 4.5 hrs | 8.4 | 50.7 | 40.9 |

This example shows that Retrol™, a clay, selectively forms more monoalkylated diphenylamine than other alkylation catalysts (e.g. AlCl$_3$). This example also shows that other alkylation catalysts form more of the less desirable disubstituted diphenylamines (having low activity on a weight basis) and leave more unsubstituted diphenylamine in the final product than clay. The unsubstituted diphenylamine is costly to remove or further react.

EXAMPLE 9

Diphenylamine (253.5 g, 1.5 mole), diisobutylene (210 g, 1.875 mole) and Retrol (7.71 g) were mixed in an autoclave and heated to 170° C. An exotherm took the temperature to 185° C. which was cooled back down to 170° C. with circulated water. After 1 hr between 170 and 185° C., gas chromatograph (GC) analysis of the reaction intermediate was 13.0% diphenylamine, 69.4% monooctyldiphenylamine and 15.3% dioctyldiphenylamine. There was 1.5% monobutyldiphenylamine and 0.85% butyloctyldiphenylamine detected. Isobutylene gas (47.7 g, 0.85 mole) was then added at 155° C.–160° C., in 1 hr. 50 minutes after the addition, the whole mixture was cooled and stripped of unreacted diisobutylene. GC showed that the liquid product contains 0.67% DPA, and 15. % DOD.

EXAMPLE 10

Diphenylamine (62 kg, 366 moles), and Retrol (2.27 kg) were mixed in an autoclave and heated to 170° C. Diisobutylene (61.73 kg, 551 moles) was added over 5 minutes. An exotherm took the temperature to 185° C. which was cooled back down to 170° C. with circulated water. After a 1 hr. reaction between 170° and 185° C., GC analysis of the reaction intermediate was 11.7% diphenylamine, 62.3% monooctyldiphenylamine and 22.0% dioctyldiphenylamine. There was 1.8% monobutyldiphenylamine and 0.8% butyloctyldiphenylamine detected. The reaction was promptly cooled to 150° C. where styrene (19.1 kg, 183 moles) was then added at 150° C.–160° C. in 5 minutes, 30 minutes after the addition, the whole mixture contains 1.0% DPA, and 17.8% DOD.

The above examples where % is equivalent to wt. % show that the process of this disclosure (clay catalyst, specific olefins, specific temperatures, and specified olefin:DPA ratios) forms desirable amounts of monosubstituted diphenylamines and lower amounts of less desirably disubstituted diphenylamines and unsubstituted diphenylamines.

The process minimizes or eliminates olefin cracking, minimizes the amount of olefins used, results in lightly colored products, uses mild conditions, may recycle or further use the clay catalyst, and provides more control over the final composition of the substituted DPA product. The process also provides a reaction product with higher antioxidant efficiency on a weight basis because the product has less unnecessary dialkyl substituents on the diphenylamine.

The antioxidants of this disclosure are useful in lubricating oils, polymers, and other hydrocarbon materials subject to oxidative degradation. Lubricating oils are well known and include mineral oils, such as those made from petroleum distillates, and synthetic ester oils, such as made from mono, di and polycarboxylic acids reacted with mono, di, or polyols in ratios such that low volatility solutions with desirable viscosities are obtained. A preferred polymer for stabilization is at least one polyol that can be used as a component in thermoplastic or thermoset polyurethanes. The at least one polyol is reacted with mono, di, or polyisocyanate compounds and the resulting urethane linkage is used as a generic name for the polymer. Polyols can be polyethers made from cyclic alkylene oxides with from 2 to 5 carbon atoms, polyesters made from di or polycarboxylic acids of from 3 to 20 carbon atoms reacted with the above alkylene oxides or di or polyhydric compounds having from 1 to 20 carbon atoms such as diethylene glycol, pentaerythritol, etc. or polyesters can be formed from the ring opening polymerization of cyclic lactones with 4 or 5 carbon atoms. Polyols can include other hydrocarbon based polymers such as polybutadiene, butadiene acrylonitrile polymers, etc. which have inherently or are reacted to have two or more hydroxyl groups thereon (e.g. either terminal, pendant or combinations thereof).

While in accordance with the patent statutes the best mode and preferred embodiment has been set forth, the scope of the invention is not limited thereto, but rather by the scope of the attached claims.

What is claimed is:

1. A process for alkylating diphenylamine, comprising:
    reacting unsubstituted diphenylamine with diisobutylene in the presence of a clay catalyst at a reaction temperature from about 105° C. to about 200° C., wherein said unsubstituted diphenylamine contains less than 20 wt. % of mono, di, and polysubstituted diphenylamines and the mole ratio of diisobutylence:unsubstituted diphenylamine is from about 1:0.5 to about 1:1.6,
    forming a mixture of diphenylamine and alkylated diphenylamines having less than 25 wt. % dioctyldiphenylamine, at least 50 wt. % monooctyldiphenylamine, and less than 25 wt. % unsubstituted diphenylamine with the proviso that the total amount of unsubstituted diphenylamine and dioctyldiphenylamine is less than 45 wt. %, and
    wherein said weight percents are based upon the total weight of said mixture of diphenylamine and alkylated diphenylamines.

2. A process according to claim 1, wherein said mixture of diphenylamine and alkylated diphenylamine includes less than 3 weight percent of monobutylmonooctyl diphenylamine.

3. A process according to claim 1, wherein the reaction temperature is from about 105° C. to about 157° C., wherein the amount of monooctyldiphenylamine is at least 60 wt. %, wherein said mole ratio of diisobutylene: unsubstituted diphenylamine is from about 1:0.7 to about 1:1.6 and wherein the amount of unsubstituted diphenylamine is less than 20 wt. %.

4. A process according to claim 3, wherein the reaction temperature is from about 110° C. to about 150° C.

5. A process according to claim 4, wherein the clay is acid activated clay.

6. A process for alkylating diphenylamine according to claim 1, wherein the reaction temperature is from about 160° C. to about 200° C. for less than 5 hours, and
    wherein the reaction product has from about 5 to less than 25 wt. % dioctyldiphenylamine, from about 50 to about 75 wt. % monooctyldiphenylamine, and from about 10 to about 25 wt. % unsubstituted diphenylamine and wherein said weight percents are based upon the total weight of said mixture of diphenylamine and alkylated diphenylamines.

7. A process according to claim 6, wherein the clay is an acid activated bentonite clay.

8. A process according to claim 6, wherein the amount of monooctyldiphenylamine is from about 55 to about 75 wt. % of the reaction mixture, the amount of dioctyldiphenylamine is from about 10 to about 20 wt. %, the amount of unsubstituted diphenylamine is from about 12 to about 20 wt. %, the amount of butyloctyldiphenylamine is less than 2 wt. % and the amount of butyldiphenylamine is less than 2 wt. %.

9. A process according to claim 8, wherein said mole ratio of diisobutylene: unsubstituted diphenylamine is from about 1:0.6 to about 1:1.2.

10. A process according to claim 1 further including a step of subsequently reacting said mixture of diphenylamine and alkylated diphenylamines with isobutylene, styrene, or alphamethylstyrene or combinations thereof in the presence of clay catalyst.

11. A process according to claim 10 wherein the isobutylene, styrene, or alpha-methylstyrene or combinations thereof are used in mole ratios of from about 1:5 to about 1:0.667 to the total diphenylamines in said mixture of diphenylamine and alkylated diphenylamines.

* * * * *